US00PP11770P2

(12) United States Plant Patent
Glicenstein

(10) Patent No.: US PP11,770 P2
(45) Date of Patent: Feb. 6, 2001

(54) CHRYSANTHEMUM PLANT NAMED 'YOCASPER'

(75) Inventor: Leon Glicenstein, State College, PA (US)

(73) Assignee: Yoder Brothers, Inc., Barberton, OH (US)

( * ) Notice: Under 35 U.S.C. 154(b), the term of this patent shall be extended for 0 days.

(21) Appl. No.: 09/270,788

(22) Filed: Mar. 17, 1999

(51) Int. Cl.[7] ..... A01H 5/00
(52) U.S. Cl. ..... Plt./289; Plt./288
(58) Field of Search ..... Plt./287, 288, 289

(56) References Cited

U.S. PATENT DOCUMENTS

P.P. 4,483 * 11/1979 Petusky ..... Plt./288

* cited by examiner

*Primary Examiner*—Howard J. Locker
(74) *Attorney, Agent, or Firm*—C. A. Whealy

(57) ABSTRACT

A distinct cultivar of Chrysanthemum plant named 'Yocasper', characterized by its upright, outwardly spreading and uniformly mounded plant habit; freely branching habit; dark green leaves; uniform and early flowering; moderately vigorous and strong plant growth; large decorative quill-type inflorescences that are about 10.5 cm in diameter when grown as a disbud; ray floret color that is initially light yellow then becoming white with subsequent development giving the inflorescence a yellow and white bi-colored appearance; and good postproduction longevity with inflorescences and leaves maintaining good substance and color for about three weeks in an interior environment.

3 Drawing Sheets

BACKGROUND OF THE INVENTION

The present invention relates to a new and distinct cultivar of Chrysanthemum plant, botanically known as *Dendranthema grandiflora* and hereinafter referred to by the cultivar name Yocasper.

The new Chrysanthemum is a product of a planned breeding program conducted by the Inventor in Salinas, Calif. The objective of the breeding program is to create new pot-type Chrysanthemum cultivars having desirable inflorescence forms and floret colors and good post-production longevity.

The new Chrysanthemum originated from a cross made by the Inventor in January, 1994, in Salinas, Calif., of a the Chrysanthemum cultivar Claro, disclosed in U.S. Plant Pat. No. 6,946 as the male, or pollen, parent, with an unidentified Chrysanthemum seedling selection as the female, or seed, parent.

The new Chrysanthemum was discovered and selected by the Inventor as a flowering plant within the progeny of the stated cross in a controlled environment in Salinas, Calif., in May, 1995. The selection of this plant was based on its desirable inflorescence form and floret colors and good post-production longevity.

Asexual reproduction of the new Chrysanthemum by terminal cuttings harvested in a controlled environment in Salinas, Calif., has shown that the unique features of this new Chrysanthemum are stable and reproduced true to type in successive generations.

SUMMARY OF THE INVENTION

The cultivar Yocasper has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yocasper'. These characteristics in combination distinguish 'Yocasper' as a new and distinct Chrysanthemum:

1. Upright, outwardly spreading and uniformly mounded plant habit.
2. Freely branching habit.
3. Dark green leaves.
4. Uniform and early flowering.
5. Moderately vigorous and strong plant growth.
6. Large decorative quill-type inflorescences that are about 10.5 cm in diameter when grown as a disbud.
7. Ray floret color that is initially light yellow then becoming white with subsequent development giving the inflorescence a yellow and white bi-colored appearance.
8. Good postproduction longevity with inflorescences and leaves maintaining good substance and color for about three weeks in an interior environment.

The new Chrysanthemum can be compared to the Chrysanthemum cultivar Phoenix, disclosed in U.S. Plant Pat. No. 8,843. However in side-by-side comparisons in Salinas, Calif., and Leamington, Ontario, Canada, under commercial practice, plants of the new Chrysanthemum differed from plants of the cultivar Phoenix in the following characteristics:

1. Plants of the new Chrysanthemum are more outwardly spreading than plants of the cultivar Phoenix.
2. Plants of the new Chrysanthemum are more vigorous than plants of the cultivar Phoenix.
3. Ray florets of the new Chrysanthemum are broader, more upright and have more open apices than ray florets of the cultivar Phoenix.
4. Ray florets of the new Chrysanthemum are initially yellow becoming white with subsequent development whereas ray florets of plants of the cultivar Phoenix are light tan in color.

BRIEF DESCRIPTIONS OF THE PHOTOGRPAHS

The accompanying colored photographs illustrate the overall appearance of the new Chrysanthemum showing the colors as true as it is reasonably possible to obtain in colored reproductions of this type.

The photograph on the first sheet comprises a top perspective view of a typical flowering plant of 'Yocasper'.

The photograph at the top of the second sheet comprises a close-up view of typical inflorescences of 'Yocasper' grown as a disbud (left) and as a spray (right).

The photograph at the bottom of the second sheet comprises a close-up view of a typical inflorescences and upper (left) and lower (right) surfaces of typical leaves.

The photograph at the top of the third sheet comprises a side view of typical flowering plants of 'Yocasper' (left) and 'Phoenix' (right).

The photograph at the bottom of the third sheet comprises a close-up view of typical inflorescences of plants of 'Yocasper' (left) and 'Phoenix' (right). Floret and foliage colors in the photographs may appear different from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown in Salinas, Calif., and Leamington, Ontario, Canada, under greenhouse conditions which approximate those generally used in commercial potted Chrysanthemum production. Four unrooted cuttings were directly stuck in a 15-cm container and pinched once. Plants used for this description were grown as disbud-types. Measurements and numerical values represent averages of typical flowering plants.

Botanical classification: *Dendranthema grandiflora* cultivar Yocasper.

Commercial classification: Decorative disbud or spray-type pot Chrysanthemum.

Parentage:

*Male or pollen parent.*—*Dendranthema grandiflora* cultivar Claro, disclosed in U.S. Plant Pat. No. 6,946.

*Female or seed plant.*—Unidentified *Dendranthema grandiflora* seedling selection.

Propagation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Herbaceous decorative quilled-type pot Chrysanthemum that can be grown as a disbud or spray. Inverted triangle; stems upright and outwardly spreading giving a uniformly mounded appearance to the plant. Freely branching; about four or five lateral branches develop after removal of terminal apex (pinching). Moderately vigorous.

*Plant height.*—About 33 cm.

*Plant width.*—About 49 cm.

*Stem color.*—Greener than 147A.

*Stem texture.*—Pubescent.

*Foliage description.*—Arrangement: Alternate. Length: About 8.7 cm. Width: About 6.6 cm. Apex: Mucronate. Base: Attenuate. Margin: Palmately lobed, sinuses between lateral lobes mostly parallel. Texture: Upper and lower surfaces with very fine pubescence; veins prominent on lower surface. Petiole length: About 2.1 cm. Color: Young foliage upper surface: Darker than 147A. Young foliage lower surface: Slightly darker than 147B. Mature foliage upper surface: Darker than 147A. Mature foliage lower surface: 147B. Venation upper surface: 147A. Venation lower surface: Close to 147B.

Inflorescence description:

*Appearance.*—Large decorative-type inflorescence form with quilled ray florets. Inflorescences borne on terminals above foliage, arising from leaf axils. Disk and ray florets arranged acropetally on a capitulum.

*Flowering response.*—Under natural conditions, plant flowers in the autumn/winter in the Northern Hemisphere. At other times of the year, inflorescence initiation and development can be induced under short day/long night conditions (at least 13.5 hours of darkness). Plants exposed to two weeks of long day/short night conditions after planting followed by photoinductive short day/long night conditions flower about eight weeks later.

*Postproduction longevity.*—Inflorescences and leaves will maintain good color and substance for about three weeks in an interior environment.

*Quantity of inflorescences.*—Grown as a disbud-type, all lateral inflorescences are removed to allow for maximum terminal inflorescence size; one inflorescence per lateral stem; about five inflorescences per plant. Grown as a spray-type, very floriferous with about nine inflorescences developing per lateral stem and about 41 inflorescences per plant.

*Inflorescence bud.*—Height: About 6 mm. Diameter: About 9 mm. Color: Close to 141A.

*Inflorescence size.*—Diameter: About 10.5 cm. Depth (height): About 2.1 cm. Diameter of disc: About 3 mm; inconspicuous.

*Ray florets.*—Shape: Elongated quill with long corolla tube. Orientation: Initially incurved, then straight and mostly flat; perpendicular to peduncle. Length: About 5.2 cm. Width at apex: About 7.5 mm. Apex: Rounded. Margin: Entire. Texture: Smooth, glabrous. Number of ray florets per inflorescence: About 182. Color: When opening: Light yellow, close to 5C. Fully opened, upper surface: White, 155D. Fully opened, lower surface: White, 155D.

*Disc florets.*—Shape: Tubular. Apex: Serrated. Length: About 6 mm. Width: About 1 mm. Number of disc florets per inflorescence: Few, about 7. Color: Immature: Greener than 154A. Mature: Apex: 9A. Midsection: Light green. Base: White.

*Reproductive organs.*—Androecium: Present on disc florets only. Anther color: 13A. Pollen: Scarce; 14A in color. Gynoecium: Present on both ray and disc florets.

Disease resistance: Resistance to known pathogens of Chrysanthemums has not been observed on plants grown under commercial greenhouse conditions.

Seed production: Seed production has not been observed.

It is claimed:

1. A new and distinct cultivar of Chrysanthemum plant named 'Yocasper', as illustrated and described.

* * * * *

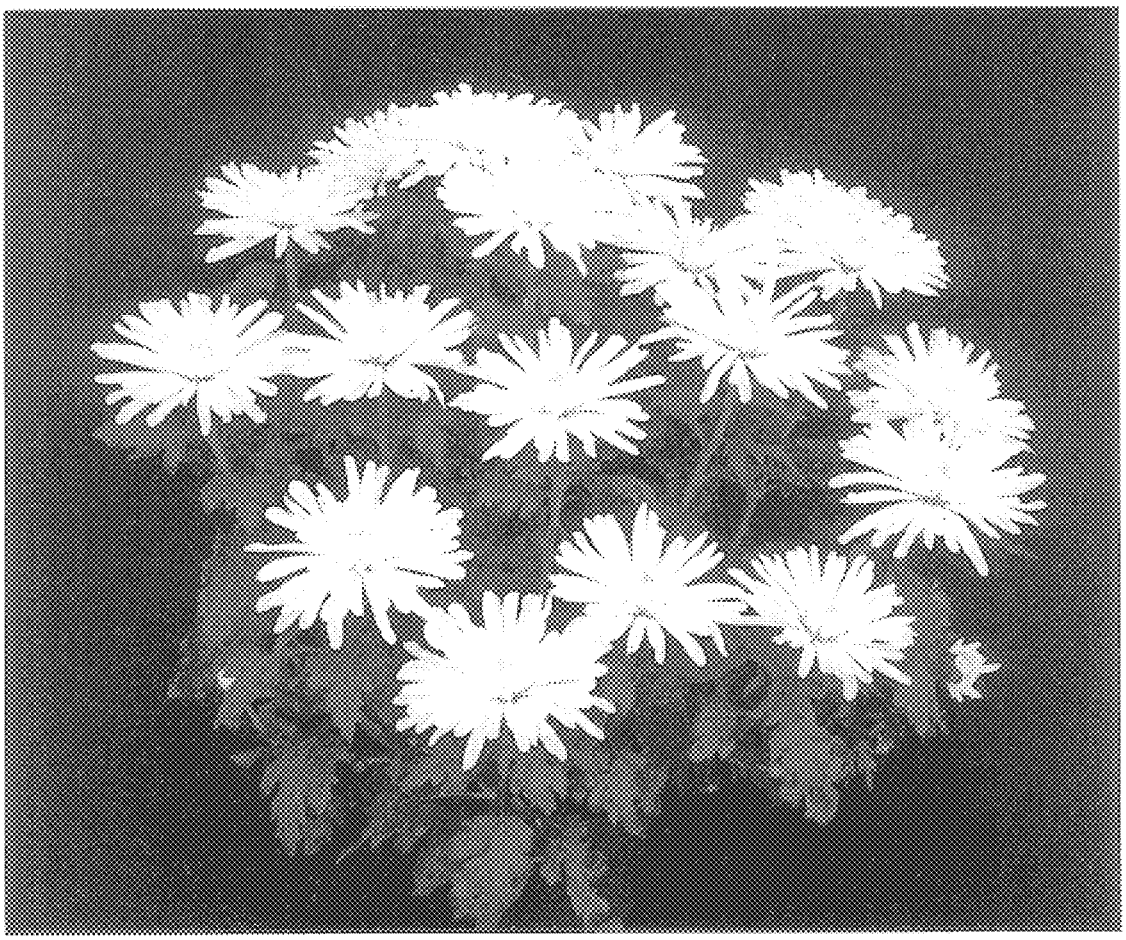

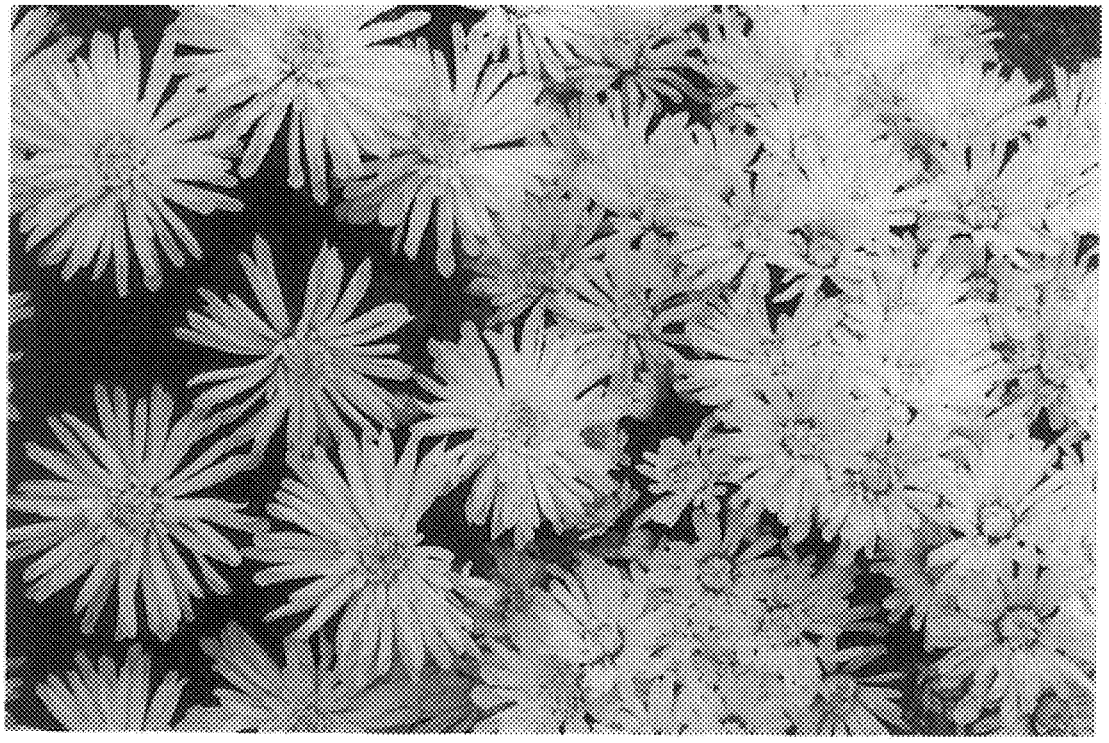
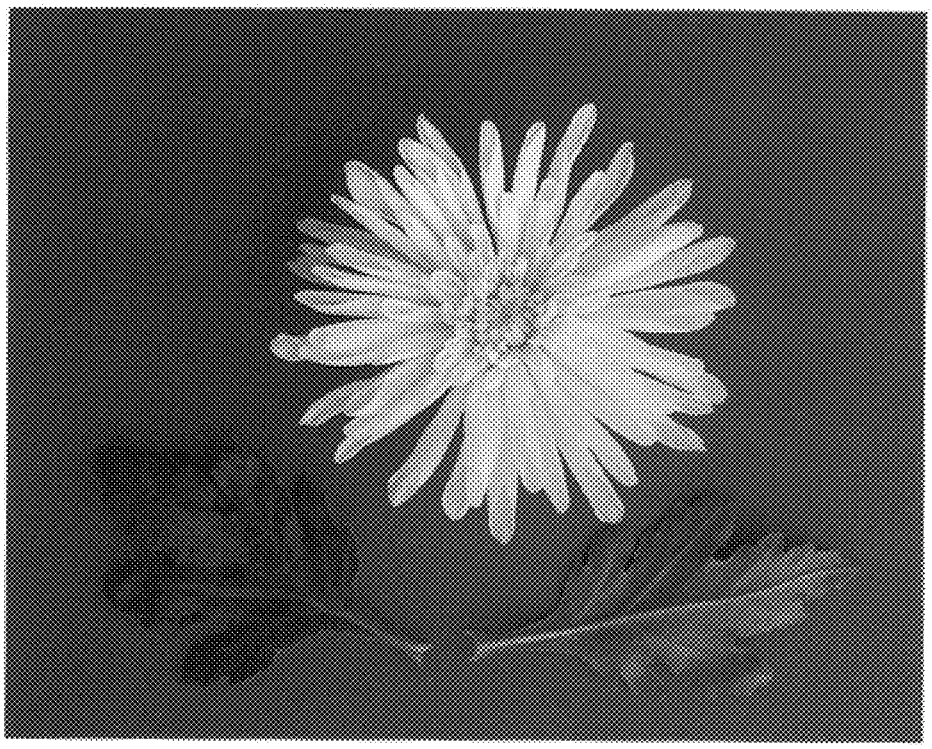

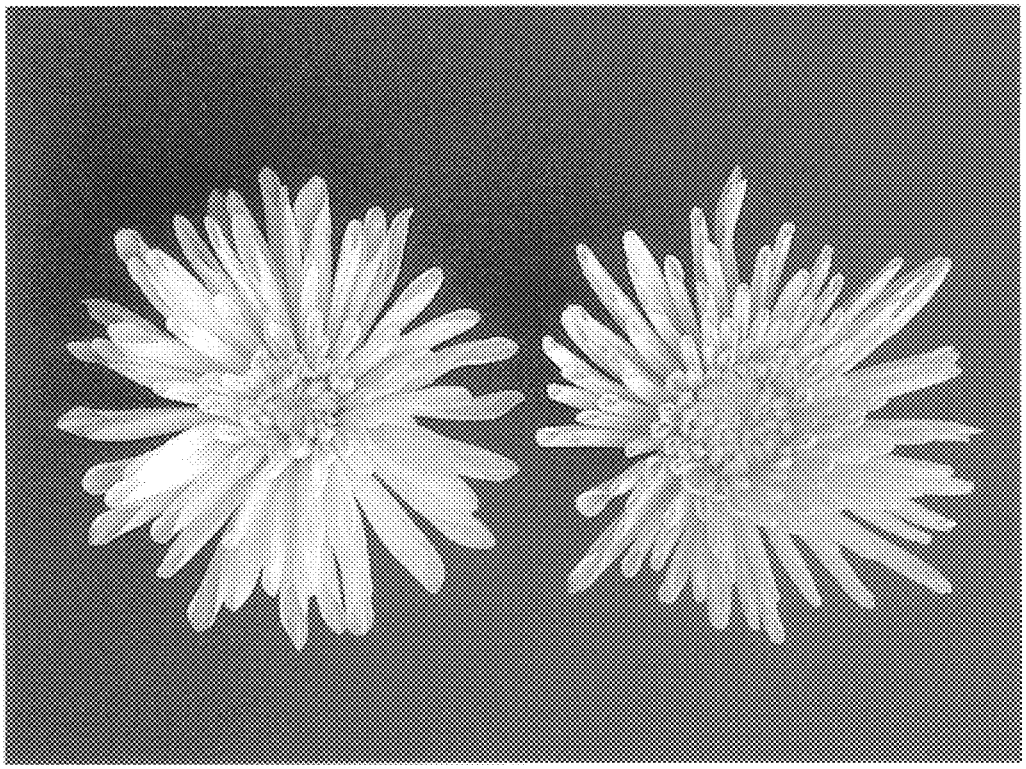

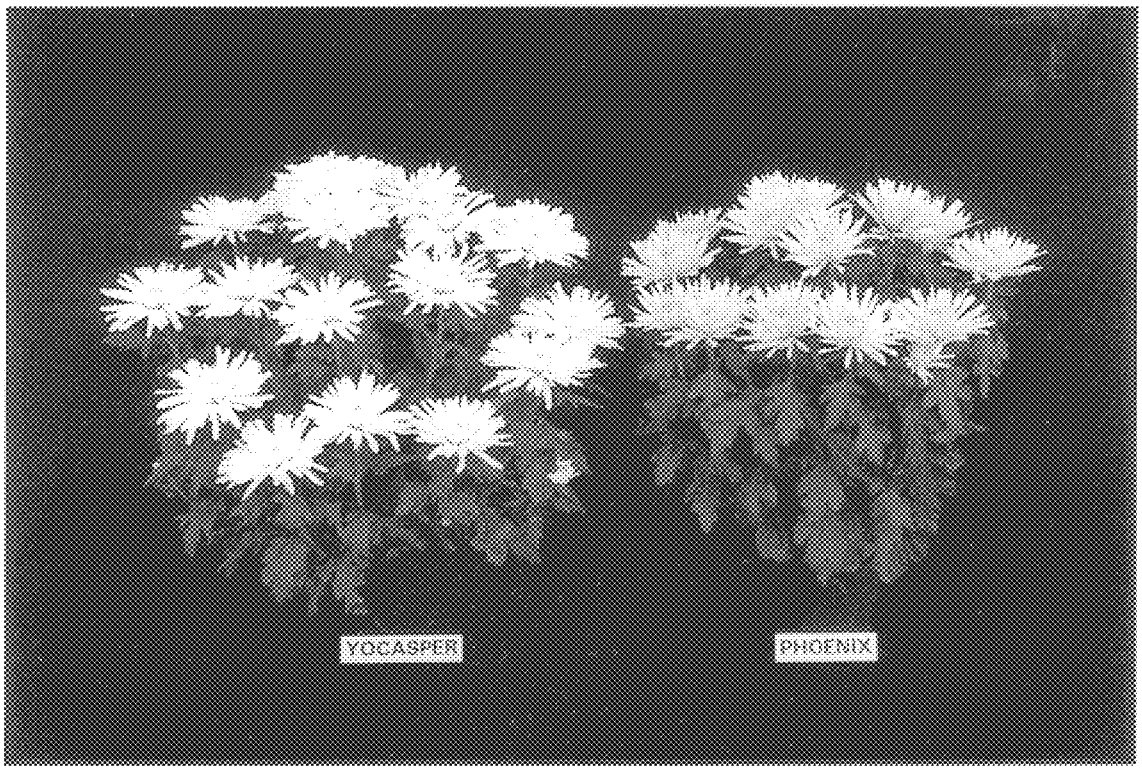
YOCASPER
PHOENIX